United States Patent
Brogna

(10) Patent No.: US 10,314,644 B2
(45) Date of Patent: Jun. 11, 2019

(54) CUT AND SEAL INSTRUMENT

(71) Applicant: INTUITIVE SURGICAL OPERATIONS, INC., Sunnyvale, CA (US)

(72) Inventor: Salvatore Brogna, Pleasanton, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 910 days.

(21) Appl. No.: 14/492,763

(22) Filed: Sep. 22, 2014

(65) Prior Publication Data

US 2015/0011996 A1 Jan. 8, 2015

Related U.S. Application Data

(60) Division of application No. 12/841,222, filed on Jul. 22, 2010, now Pat. No. 8,858,547, which is a
(Continued)

(51) Int. Cl.
*A61B 18/14* (2006.01)
*A61B 17/00* (2006.01)
(Continued)

(52) U.S. Cl.
CPC .. *A61B 18/1445* (2013.01); *A61B 2017/0046* (2013.01); *A61B 2017/0088* (2013.01);
(Continued)

(58) Field of Classification Search
CPC .. A61B 2018/1495; A61B 2018/00773; A61B 18/1442
See application file for complete search history.

(56) References Cited

U.S. PATENT DOCUMENTS 5,391,166 A 2/1995 Eggers
5,395,369 A * 3/1995 McBrayer ............. A61B 17/29
600/564
(Continued)

FOREIGN PATENT DOCUMENTS

WO WO-2008045350 A2 4/2008

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Jaymi E Della
(74) *Attorney, Agent, or Firm* — Jones Robb, PLLC

(57) ABSTRACT

A surgical system including a cartridge having a first tissue sealing electrode and a surgical instrument including a first jaw and a second jaw, wherein the first jaw comprises a second tissue sealing electrode facing the second jaw, and wherein the second jaw is configured to removably receive the cartridge in a position where the first tissue sealing electrode is opposite the second tissue sealing electrode. The surgical system further includes a cut and seal controller, wherein the cut and seal controller automatically generates a command to the surgical instrument to reduce a clamping force between the first and the second jaws after sensing that tissue sealing is complete.

16 Claims, 8 Drawing Sheets

Related U.S. Application Data continuation-in-part of application No. 12/705,418, filed on Feb. 12, 2010, now abandoned.

(60) Provisional application No. 61/157,554, filed on Mar. 5, 2009.

(51) Int. Cl.
  *A61B 18/00* (2006.01)
  *A61B 90/00* (2016.01)

(52) U.S. Cl.
  CPC ............... *A61B 2018/0063* (2013.01); *A61B 2018/00107* (2013.01); *A61B 2018/00988* (2013.01); *A61B 2018/1412* (2013.01); *A61B 2018/1455* (2013.01); *A61B 2018/1495* (2013.01); *A61B 2090/0803* (2016.02)

(56) References Cited

U.S. PATENT DOCUMENTS

| | | | | |
|---|---|---|---|---|
| 5,507,297 | A | 4/1996 | Slater et al. | |
| 5,573,535 | A * | 11/1996 | Viklund | A61B 18/1442 606/37 |
| 5,611,808 | A | 3/1997 | Hossain et al. | |
| 5,891,142 | A | 4/1999 | Eggers et al. | |
| 5,951,549 | A | 9/1999 | Richardson et al. | |
| 6,050,996 | A | 4/2000 | Schmaltz et al. | |
| 6,174,309 | B1 * | 1/2001 | Wrublewski | A61B 18/1442 606/45 |
| 6,312,435 | B1 | 11/2001 | Wallace et al. | |
| 6,491,701 | B2 | 12/2002 | Tierney et al. | |
| 6,817,974 | B2 | 11/2004 | Cooper et al. | |
| 6,991,627 | B2 | 1/2006 | Madhani et al. | |
| 7,033,356 | B2 | 4/2006 | Latterell et al. | |
| 7,041,102 | B2 | 5/2006 | Truckai et al. | |
| 7,137,980 | B2 | 11/2006 | Buysse et al. | |
| 7,320,700 | B2 | 1/2008 | Cooper et al. | |
| 7,442,193 | B2 | 10/2008 | Shields et al. | |
| 7,632,269 | B2 | 12/2009 | Truckai et al. | |
| 8,640,788 | B2 | 2/2014 | Dachs, II et al. | |
| 8,852,174 | B2 | 10/2014 | Burbank | |
| 8,858,547 | B2 | 10/2014 | Brogna | |
| 2002/0128649 | A1 * | 9/2002 | Bacher | A61B 18/1445 606/46 |
| 2002/0151889 | A1 * | 10/2002 | Swanson | A61B 18/1482 606/41 |
| 2002/0165531 | A1 * | 11/2002 | Goble | A61B 18/1445 606/40 |
| 2003/0018331 | A1 * | 1/2003 | Dycus | A61B 18/1445 606/48 |
| 2003/0114851 | A1 * | 6/2003 | Truckai | A61B 18/1445 606/51 |
| 2004/0260279 | A1 * | 12/2004 | Goble | A61B 18/12 606/34 |
| 2005/0113821 | A1 * | 5/2005 | Pendekanti | A61B 17/072 606/41 |
| 2005/0159745 | A1 * | 7/2005 | Truckai | A61B 18/1442 606/51 |
| 2005/0240178 | A1 * | 10/2005 | Morley | A61B 18/1445 606/51 |
| 2007/0023477 | A1 | 2/2007 | Whitman et al. | |
| 2007/0173811 | A1 * | 7/2007 | Couture | A61B 18/1445 606/39 |
| 2007/0179499 | A1 | 8/2007 | Garrison | |
| 2008/0009860 | A1 * | 1/2008 | Odom | A61B 18/1445 606/51 |
| 2008/0015566 | A1 | 1/2008 | Livneh | |
| 2008/0021450 | A1 | 1/2008 | Couture | |
| 2008/0154299 | A1 | 6/2008 | Livneh | |
| 2008/0208246 | A1 | 8/2008 | Livneh | |
| 2009/0095790 | A1 | 4/2009 | Whitman et al. | |
| 2009/0138006 | A1 * | 5/2009 | Bales | A61B 18/1206 606/33 |
| 2009/0157071 | A1 | 6/2009 | Wham et al. | |
| 2009/0157074 | A1 * | 6/2009 | Livneh | A61B 18/1445 606/37 |
| 2010/0089970 | A1 | 4/2010 | Smith et al. | |
| 2010/0228250 | A1 | 9/2010 | Brogna | |
| 2011/0009859 | A1 | 1/2011 | Livneh | |
| 2011/0118707 | A1 | 5/2011 | Burbank | |
| 2011/0118708 | A1 | 5/2011 | Burbank et al. | |
| 2011/0118709 | A1 | 5/2011 | Burbank | |
| 2012/0209263 | A1 | 8/2012 | Sharp et al. | |
| 2013/0018372 | A1 | 1/2013 | Sims et al. | |
| 2013/0282023 | A1 | 10/2013 | Burbank et al. | |

\* cited by examiner

CUT AND SEAL INSTRUMENT

CROSS REFERENCE TO RELATED APPLICATIONS

This application is a divisional application of U.S. patent application Ser. No. 12/841,222 (filed Jul. 22, 2010, currently pending), which is a continuation-in-part of U.S. patent application Ser. No. 12/705,418 (filed Feb. 12, 2010, now abandoned), which claims the benefit of priority of U.S. Provisional Patent Application No. 61/157,554 (filed Mar. 5, 2009), the entire contents of each of which are incorporated herein by reference.

BACKGROUND

1. Field of Invention

Aspects of the invention pertain to surgical instruments, more particularly to instruments used during minimally invasive surgery, and still more particularly to instruments used to perform tissue sealing and cutting.

2. Art

During a surgical procedure, certain tissues such as blood vessels are first sealed before they are cut (bisected). One way to do this is with clamps. At least two clamps are applied to the vessel, and then the vessel is cut between the clamps. Another way to seal tissue (e.g., intestines) is with a stapler. Surgical staplers typically apply at least two staple rows on either side of a line to be cut. Such staplers use single-use staple cartridges, and often a cutting blade is mounted in the cartridge. A more effective way than clamping or stapling to seal tissue is by using radio frequency (RF) energy. An illustrative instrument used for such RF sealing is the LigaSure™ Atlas™ instrument available from Valley-Lab, a Covidien Ltd. division. A disadvantage of such tissue sealing instruments is their limited lifespan, because the sealing electrodes deteriorate quickly with use. Typically, an entire RF sealing instrument is disposed of after a single surgical operation.

During minimally invasive surgical procedures (e.g., laparoscopy, either manual or robotically assisted), a surgeon may be required to manipulate tissue with two or more grasping instruments, and then remove one grasping instrument to allow a sealing instrument to be inserted. And so a surgeon may need to remove a grasping instrument to insert a sealing instrument, and then remove the sealing instrument to insert a cutting instrument, thus further slowing the surgery.

Further, the surgeon often has no indication that an acceptable clamping pressure exists between the sealing instrument jaws. Surgeons using manual instruments typically learn to judge by feel when an acceptable clamping pressure is reached, but they rely on a successful post facto tissue sealing indication from an associated electro-surgical unit to know that they used an acceptable clamping pressure. In a telerobotic surgical system context, however, such a clamping pressure indication may not be available, and in a manual context, there is a risk that a surgeon has not achieved the correct clamping force.

Therefore, what is required is a cost effective surgical instrument that performs both tissue cutting and sealing. What is further required is an instrument capable of grasping and manipulating tissue in addition to tissue cutting and sealing. And in addition, it is desirable to provide closed loop feedback that indicates that an acceptable clamping pressure exists before the sealing procedure is initiated.

SUMMARY

In accordance with aspects of the invention, a surgical instrument combines tissue cutting and sealing functions. The distal end of the instrument has two opposing jaw members that clamp the tissue to be sealed and cut. In one illustrative embodiment, one of the jaw members is movable and the other is stationary. The movable jaw member includes a tissue sealing electrode. The stationary jaw member has a removable cartridge, and the cartridge includes another tissue sealing electrode and a tissue cutter. When the jaw members clamp tissue to be sealed and cut between them, tissue sealing energy directed to the tissue sealing electrodes seals across the tissue in two lines. After sealing is complete, the tissue cutter cuts the tissue between the two seal lines. The cartridge may be used once, or it may be used two or more times. Accordingly, only the cartridge is disposed of, and the main portion of the combined tissue cutting and sealing instrument may be used many times.

In accordance with another aspect of the invention, the tissue cutter in the cartridge is returned to its starting position to allow the cartridge to be reused two or more times for tissue sealing and cutting.

In accordance with other aspects of the invention, a cutting and sealing controller automatically initiates tissue cutting after sensing that tissue sealing is complete. Further, the cutting and sealing controller may automatically release tissue clamping pressure after sensing that either tissue sealing or tissue cutting is complete.

In accordance with other aspects of the invention, a combined cutting and sealing instrument is configured to grasp tissue.

In accordance with still other aspects of the invention, pressure sensors sense the clamping pressure to determine if an acceptable pressure exists for effective tissue sealing. The pressure indications may be used to prevent premature sealing, or to automatically initiate various actions associated with sealing.

DETAILED DESCRIPTION

This description and the accompanying drawings that illustrate aspects and embodiments of the present invention should not be taken as limiting—the claims define the protected invention. Various mechanical, compositional, structural, electrical, and operational changes may be made without departing from the spirit and scope of this description and the claims. In some instances, well-known circuits, structures, and techniques have not been shown or described in detail in order not to obscure the invention. Like numbers in two or more figures represent the same or similar elements.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes includes various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

In general, aspects and embodiments are described in the context of telerobotic surgical systems, such as the da Vinci® Surgical Systems developed and commercialized by Intuitive Surgical, Inc. of Sunnyvale, Calif. Skilled persons will understand that such aspects and embodiments are not limited to the da Vinci® Surgical Systems, or even to robotic systems, and may be applicable to, e.g., hand held and hand actuated mechanisms.

Aspects and embodiments are described in terms of tissue sealing. It should be understood that this term includes any fusing together of tissue.

Figure 1:
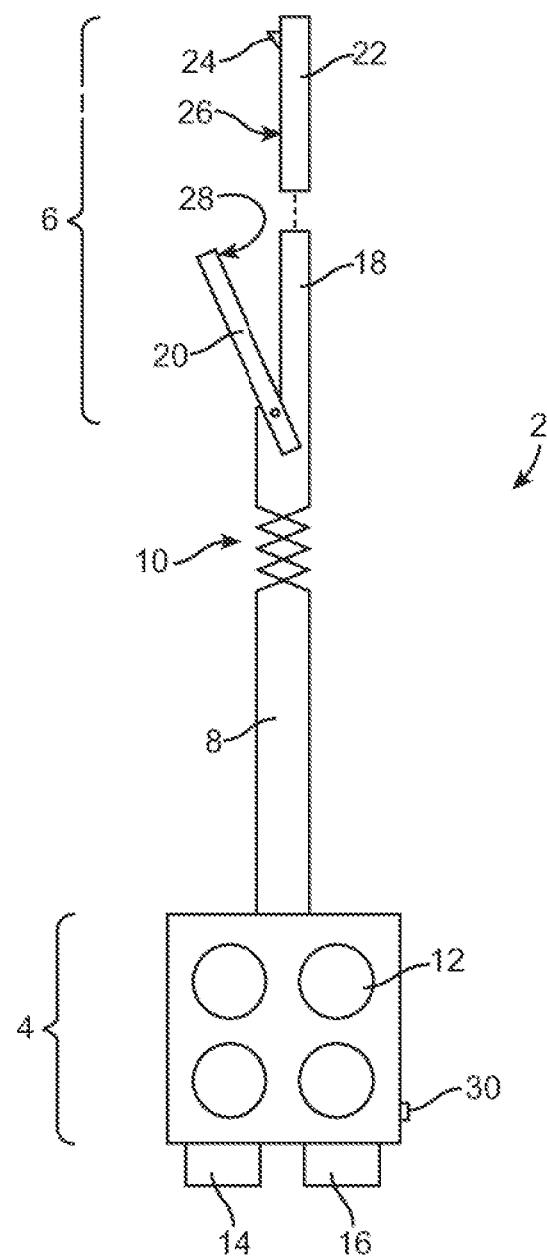
FIG. 1 is a diagrammatic view of a cut and seal surgical instrument.

FIG. 1 is a diagrammatic view of a cut and seal surgical instrument 2 in accordance with an aspect of the invention. As shown in FIG. 1, instrument 2 includes a force transmission mechanism 4 at the proximal end (outside the patient) and a combined cut and seal end effector 6 at the distal end (inside the patient; closer to the surgical site). Transmission mechanism 4 and cut and seal end effector 6 are coupled by instrument shaft 8. Cut and seal end effector 6 is optionally coupled to instrument shaft 8 via wrist mechanism 10. Instrument 2 is typically used to carry out minimally invasive surgery, during which end effector 6 and a distal part of shaft 8 are inserted into a patient via a small incision or natural orifice, typically through a cannula, to carry out a surgical procedure.

In the depicted embodiment, force transmission mechanism 4 includes disks 12, which mate to corresponding servomotors (not shown) when instrument 2 is mounted, e.g., for use in a surgical robotic system (described in more detail below). The servomotors provide actuating forces to move components of instrument 2. Four disks 12 are shown; more or fewer may be used, depending on the desired actuated degrees of freedom for instrument 2. The servomotors are controlled by a surgeon moving a master manipulator, as described in more detail below. In addition, one or more servomotors 14,16 may be mounted on instrument 2 itself to provide actuating forces for instrument 2 components.

Shaft 8 is generally a hollow tube through which actuating cables run from transmission mechanism 4 to the components at the distal end of instrument 2. Such cables are illustrative of various ways (e.g., rods, rotating shafts, and the like) of moving instrument components. In some embodiments, shaft 8 rotates to provide roll to end effector 6. Shaft 8, and end effector 6, may have various outer diameters (e.g., 5 mm, 8 mm, 10 mm, 12 mm, etc.). Although shaft 8 is depicted as rigid, it is also illustrative of various flexible embodiments that may be used.

Optional wrist mechanism 10, when used, provides one or more additional degrees of freedom (e.g., pitch, yaw, pitch and yaw, etc.) for end effector 6. Various wrist mechanism configurations may be used. See e.g., U.S. Pat. No. 6,312,435 (filed Oct. 8, 1999), U.S. Pat. No. 6,491,701 (filed Jan. 12, 2001), U.S. Pat. No. 6,817,974 (filed Jun. 23, 2002), U.S. Pat. No. 6,991,627 (filed Feb. 15, 2002), U.S. Pat. No. 7,320,700 (filed Dec. 2, 2003); U.S. Patent Application Pub. No. US 2007/0023477 A1 (filed Jul. 27, 2005); and U.S. Patent Application Nos. 61/260,903 (filed Nov. 13, 2009), 61/260,910 (filed Nov. 13, 2009), 61/260,915 (filed Nov. 13, 2009), and 61/760,919 (filed Nov. 13, 2009), all of which are incorporated herein by reference, for various illustrative wrist mechanisms.

In the embodiment depicted in FIG. 1, cut and seal end effector 6 includes a stationary jaw member 18, a movable jaw member 20, and a removable cut and seal cartridge 22 that is removably coupled to stationary jaw member 18. Tissue is clamped between jaws 18 and 20 for cutting and sealing. Cut and seal cartridge 22 includes a movable tissue cutter 24 (i.e., a sharp blade). Movable jaw member 20 may be actuated via a force transmitted through force transmission mechanism 4, or it may be actuated by one of the motors 14,16 mounted on instrument 2. Similarly, tissue cutter 24 may be actuated via a force transmitted through force transmission mechanism 4 or by one of the motors 14,16. In one aspect, a single motor 14 or 16 may be used to actuate both jaw 20 and tissue cutter 24. In one alternate aspect, jaw 18 may be movable and jaw 20 stationary, such that cartridge 22 is moved during instrument operation. In another alternate aspect, both jaws 18 and 20 are moveable.

End effector 6 also includes tissue sealing capability. A first tissue sealing electrode 26 is positioned on the inner face of cartridge 22. A second tissue sealing electrode 28 is positioned on jaw 20, opposing electrode 26. The electrodes 26,28 are described in more detail below. Electrical energy for tissue sealing is provided to electrodes 26,28 via an electrical coupling 30 at the proximal end of instrument 2. Electrical coupling 30 as depicted in FIG. 1 is illustrative of various positions at which it may be placed on the instrument, and it may require manual coupling to a tissue sealing energy source or it may couple automatically to the energy source when instrument 2 is mounted to a robotic manipulator for surgical operation.

Figure 2:
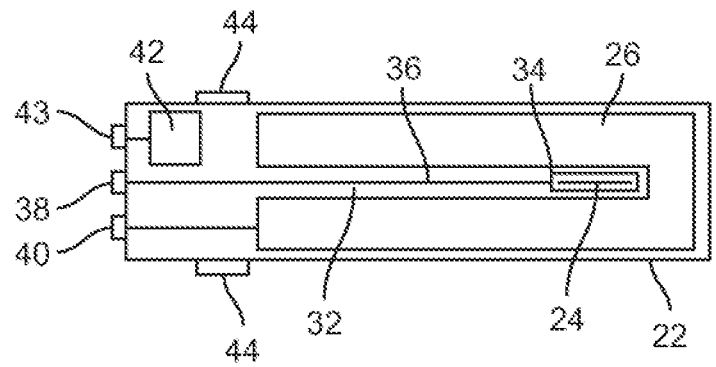
FIG. 2 is a diagrammatic top view of removable cut and seal cartridge.

FIG. 2 is a diagrammatic top view of removable cut and seal cartridge 22. Electrode 26 is depicted in an elongated "U" shape so that it surrounds a slot 32 through which tissue cutter 24 moves. Various other electrode shapes of configurations may be used. In many aspects electrode 26 is positioned on both sides of slot 32 so that both free ends of a cut tissue (e.g., a blood vessel) are sealed before the tissue is cut between the two seals. Electrode 26 receives electrical sealing energy via electrical coupling 40, which mates with a corresponding electrical coupling when cartridge 22 is inserted into instrument 2.

FIG. 2 also shows that tissue cutter 24 is mounted on a sled 34 that moves as lead screw 36 rotates. Lead screw 36 is attached to a mechanical coupling 38 it the proximal end of cartridge 22, and coupling 38 attaches to a drive shaft when cartridge 22 is installed in instrument 2. Details of the coupling are described below. As described herein, tissue cutter 24 moves proximally to cut tissue. It is well understood, however, that tissue cutter 24 may move distally to perform its cutting action using a similar sled and lead screw operating mechanism.

In one aspect, the depicted tissue cutter 24 and slot 32 are illustrative of a stationary electrode that is used to bisect tissue. That is, the one electrode 26 is used to seal the tissue along two adjacent lines, and a second electrode that receives electrical energy is used to bisect the tissue between the sealed lines.

FIG. 2 also shows that in some aspects cartridge 22 includes an electronic encryption device 42 (e.g., integrated circuit with data storage capability; in practice this is sometimes referred to as a "Dallas chip"). Electronic encryption device 42 may be used to convey information to the cut and seal control system (see below) about the cartridge type, if the cartridge has been used (to enforce one-time use restrictions), or the number of available lives for use (to manage multiple use restrictions (e.g., three uses)). Electronic encryption device 42 may also be used to ensure that a properly manufactured cartridge is being used. Electrical coupling 43 provides a connection point for encryption device 42.

FIG. 2 also shows two snap fittings 44, which are illustrative of various ways of securely yet removably fastening removable cut and seal cartridge 22 in instrument 2.

Figure 3A:
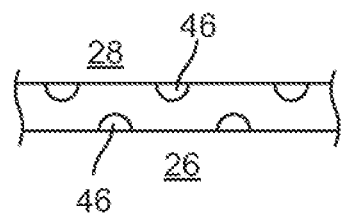
FIGS. 3A and 3B are diagrammatic cross-sectional views of electrode configurations.
Figure 3B:
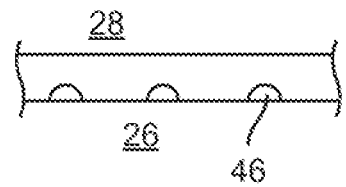

FIGS. 3A and 3B are diagrammatic cross-sectional views of electrode configurations. As shown in. FIG. 3A, the opposing surfaces of both electrode 26 (on cartridge 22) and electrode 28 (on the opposing jaw member) include small, ceramic, insulating "dots" 46 over electrically conductive stainless steel. The use of various combinations of insulating ceramic and electrical conductors in tissue sealing electrodes is known (e.g., as used in LigaSure™ Atlas™ sealing devices). As shown in FIG. 3B, the insulating "dots" 46 are placed only on electrode 26. Placing the ceramic only on the cartridge electrode 26 may avoid some manufacturing expense in embodiments in which the jaw electrode is used many times with two or more different cartridges when the use of ceramic on a single electrode is sufficient, and yet the ceramic must be in good condition and not degraded from multiple uses.

Figure 4:
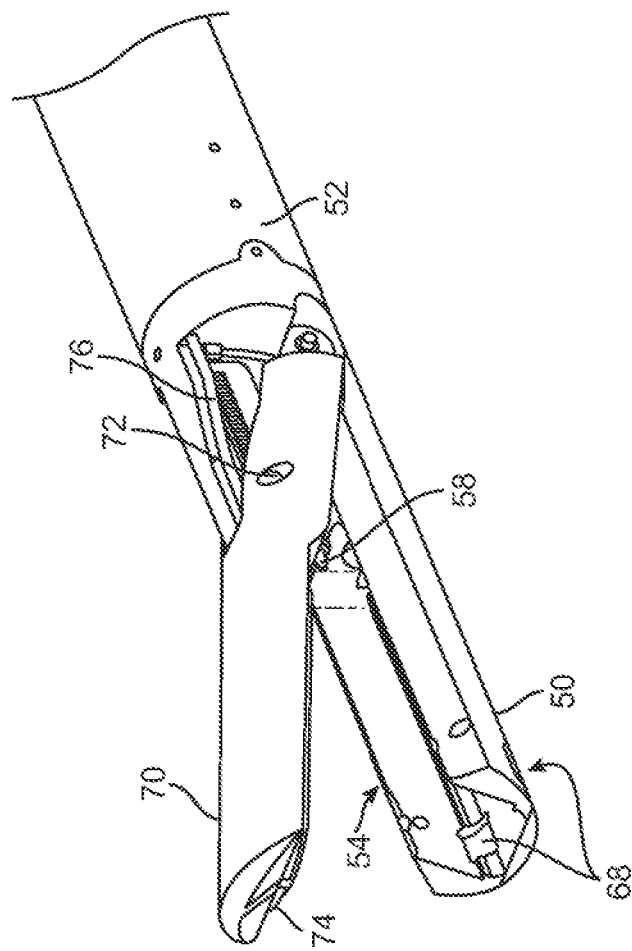
FIG. 4 is a perspective view of an embodiment of the distal end of a combined cut and seal minimally invasive surgical instrument.
Figure 4:
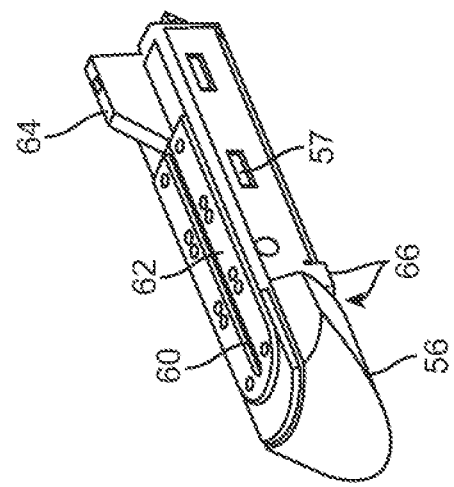

FIG. 4 is a perspective view of another embodiment of the distal end of a combined cut and seal minimally invasive surgical instrument, generally described above as end effector 6. FIG. 4 shows stationary jaw member 50 coupled to instrument shaft 52 (the optional wrist mechanism is omitted fear clarity). A channel 54 in jaw member 50 receives removable cut and seal cartridge 56. Matching guide rails 57 and grooves (not shown) may be used in channel 54 and on cut and seal cartridge 56 to improve alignment and secure mounting. An illustrative electrical coupling 58 for cut and seal cartridge 56 is shown at the proximal end of channel 54 (in this perspective view, the mechanical and other electrical couplings are hidden). As cartridge 56 is secured in position within channel 54, the necessary electrical and mechanical couplings are automatically made.

As shown in FIG. 4, cut and seal cartridge 56 includes a tissue sealing electrode 60 that receives electrical tissue sealing energy via the electrical coupling in channel 54. A slot 62 in electrode 60 allows a tissue cutter (not shown) to rise above electrode 60's surface and move proximally to cut tissue clamped between the jaw members. A raised tab 64 at the proximal end of cartridge 56 provides additional contact area for electrical connections, as well as a safety position. for the tissue cutter, as described below. Fittings 66 (one is hidden) hold cartridge 56 in place in corresponding detents 68 in jaw member 50.

Movable jaw member 70 is coupled at hinge 72. Tissue sealing electrode 74 is shaped and positioned on jaw member 70 so that it is aligned with cut and seal cartridge electrode 60 when the cartridge is secured in channel 54. Electrode 74, and jaw member 70, includes a slot (not shown) to allow the tissue cutter in cartridge 56 to extend into jaw member 70 during cutting operations. Electrode 74 receives tissue sealing energy via a wire 76, which is routed through shaft 52 and in turn receives energy via a coupling at the proximal end of the instrument, as described above.

Figure 5:
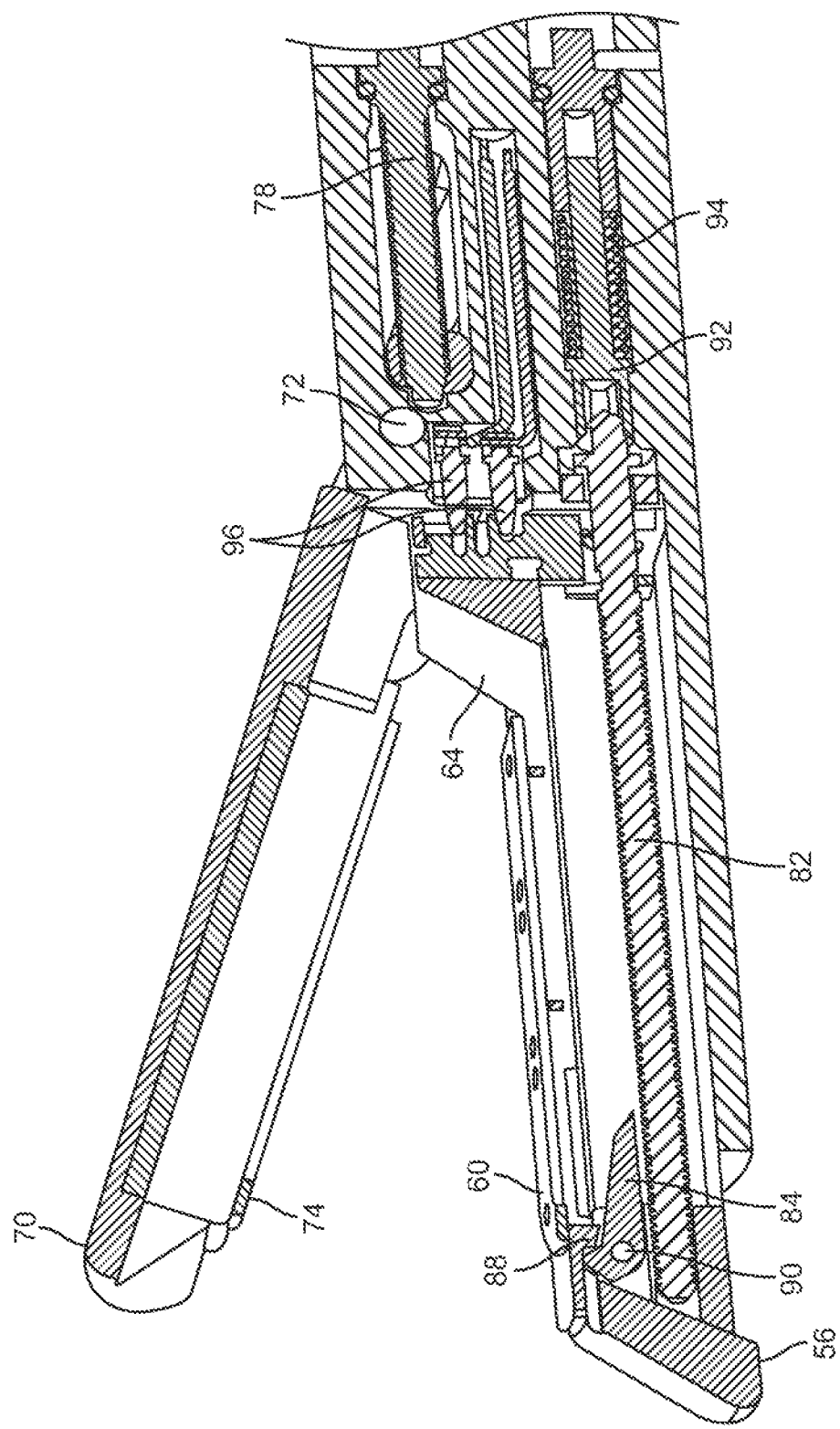
FIG. 5 is a side cross-sectional view of the embodiment depicted in FIG. 4.

FIG. 5 is a side cross-sectional view of the embodiment depicted in FIG. 4, with the cut and seal cartridge securely positioned in the stationary jaw member. The embodiment shown in FIG. 5 is illustrative of working aspects of the distal end of the combined cut and seal minimally invasive surgical instrument.

As shown in FIG. 5, a first lead screw 78 operates movable jaw member 70. As lead screw 78 rotates (actuated, e.g., by one of the motors 14,16 (see FIG. 1)), sliding member travels proximally and jaw member 70 moves towards jaw member 50 to clamp tissue in between them. The use of the lead screw provides the strong clamping force required for effective tissue sealing and cutting. When the tissue is clamped with sufficient force (clamping force feedback or other feedback may be used), the sealing and cutting operations may begin. During sealing, electrodes 60 and 74 receive electrical sealing energy to seal the clamped tissue. When sealing is complete, tissue cutting may begin.

A second lead screw 82 inside cut and seal cartridge 56 operates tissue cutter 84. As lead screw 82 rotates, the sled moves tissue cutter 84 (i.e., sharp blade) proximally to cut the tissue clamped between the jaw members. As tissue cutter 84 starts to move, it engages tab 88, which causes tissue cutter 84 to rotate around hinge 90 and extend beyond the clamping surfaces of electrodes 60 and 74. Other ways of keeping the tissue cutting blade safe include, for example, surrounding it in a small raised covering when not in use. Tab 64 provides a safety position for tissue cutter 84 after it moves to its proximal position.

In some aspects, after tissue cutter 84 has cut tissue, lead screw 82 may be rotated in the opposite direction to return tissue cutter 84 to its distal, ready to cut position. In this way, the cutting feature of removable cut and seal cartridge 56 may be reused, so that both the cutting and sealing operations may be performed more than once with a single cartridge. Such multiple use has a significant cost saving benefit.

Lead screw 82 is coupled to receive mechanical power (e.g., from one of motors 14,16 (see FIG. 1)) via mechanical coupling 92. Mechanical coupling 92 includes a spring 94 that forces the coupling distally. When removable cut and seal cartridge 56 is first fully inserted into jaw member 50, the mating mechanical couplings on the cartridge and in the jaw member may not be aligned (e.g., splines or various shapes may not be aligned). The force provided by spring 94 will move the instrument side coupling to fully engage the cartridge coupling as soon as it rotates into proper alignment.

FIG. 5 also shows two additional electrical contacts 96 that electrically contact corresponding contacts on raised tab 64 on cut and seal cartridge 56. These contacts are used to provide electrical connection to the electronic encryption device (not shown; see FIG. 2) in cartridge 56.

Figure 6:
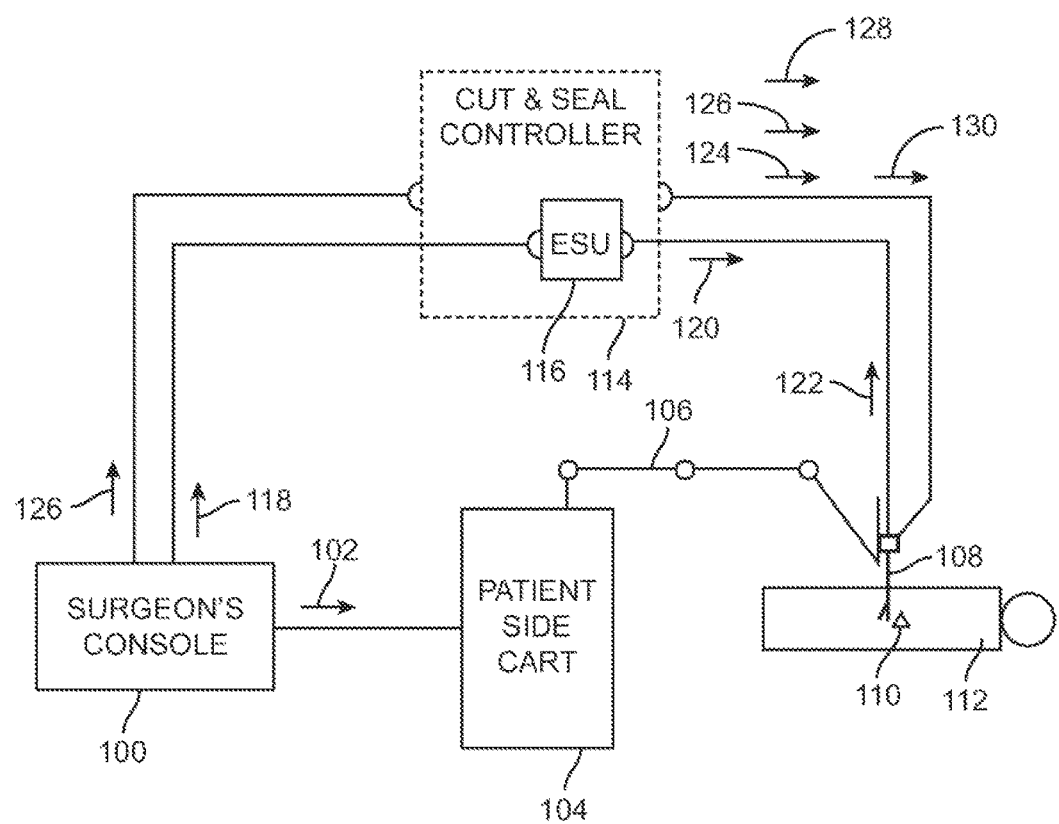
FIG. 6 is a diagrammatic view of a combined tissue cutting and sealing system.

FIG. 6 is a diagrammatic view of a combined tissue cutting and sealing system implemented on a minimally invasive surgical robotic system (e.g., a da Vinci® Surgical System). The components shown in FIG. 6 are illustrative of various similar components in other robotic systems, and some automated aspects may be used in either robotic or non-robotic embodiments. Various system components are omitted so as to more clearly illustrate the inventive aspects.

In the telerobotic system shown in FIG. 6, a surgeon operates master controls at surgeon's console 100. In response to the surgeon's master control movements, control signals 102 are output to patient side cart 104, which includes a servo controlled kinematic arm 106. A combined cut and seal instrument 108 as described herein is mounted at the end of arm 106 and becomes part of a slave side kinematic chain slaved to the surgeon's master input movements. Thus, the surgeon is capable of telerobotically moving instrument 108 to perform a surgical act at surgical site 110 inside patient 112.

FIG. 6 also shows a cut and seal controller 114 that controls specific cut and seal aspects of the cut and seal instrument 108 in accordance with aspects of the invention. Cut and seal controller 114 is depicted in dotted line to illustrate that its functions may be in a discrete unit, may be combined with another electronic data processing unit in the system, or may be distributed among two or more electronic data processing units in the system. The cut and seal controller functions may be carried out in software or firmware or other known methods. For this detailed description, the cut and seal controller 114 is considered to include an electro-surgical unit (ESU) 116. Examples of such ESUs ate LigaSure™ vessel sealing generators, such as the LigaSure™ ForceTriad™ energy platform (available from ValleyLab, a division of Covidien Ltd.).

To carry out a procedure, the surgeon first moves instrument 108 into position at surgical site 110 and clamps tissue (e.g., a blood vessel) to be sealed and cut. When the proper clamping force is achieved (automatically or under the surgeon's control), the surgeon commands the sealing operation to begin by sending a signal 118 to ESU 116. In turn, ESU 116 sends sealing energy 120 to instrument 108's electrodes, described above. When ESU senses that sealing is complete (e.g., by impedance measurement 122 at the tissue being sealed), it automatically shuts off sealing energy 120.

In accordance with an aspect of the invention, when the ESU shuts off sealing energy 120, cut and seal controller 114 automatically generates a signal 124 to instrument 108 to begin the cutting operation without the surgeon commanding a separate cut command. Thus the combined cutting and sealing is carried out with a single command 126 from the surgeon because the cut and seal controller controls both cutting and sealing aspects of instrument 108. In additional aspects of the invention, cut and seal controller may automatically send a signal 126 to instrument 108 to either loosen or release the clamping force and/or may automatically send a signal 128 to instrument 108 to reset the tissue cutter in preparation for another combined cut and seal act. The cut and seal controller 114 may command various combinations or all of these automatic actions in response to a single command signal 126 from the surgeon. Further, the cut and seal controller may issue updated information 130 to the electronic encryption device in instrument 108 to effectively manage use restrictions, as described above.

Using two opposing removable cartridges for sealing, one in each opposing jaw member, at least one cartridge having tissue cutting capability, is within the aspects of the present invention. In other aspects of the invention, the cutting feature may be omitted, and so a single removable cartridge with a sealing electrode may be positioned in either a stationary or movable jaw, or opposing removable cartridges may be positioned in opposing stationary/moving or moving/moving jaw architectures.

Various commercial ESU's are available. Each ESU typically has a proprietary method of determining when a proper tissue seal has been formed. For example, electrical impedance may be measured between the electrodes during the sealing operation, and sealing may be terminated once a particular impedance value is detected. In addition, certain sealing instrument jaw configurations (e.g., the geometry (two- or three-dimensional) of the electrode surface that contacts tissue) may be associated with particular ESU's, so that certain sealing instruments may be used only with certain associated ESU's. That is, one company's instrument electrode geometry may be designed to work optimally with that company's ESU, and a second company's instrument electrode geometry may be designed to work optimally with the second company's ESU. Consequently, medical personnel may have to have various different sealing instruments available to be used with various ESU's.

Figure 7:
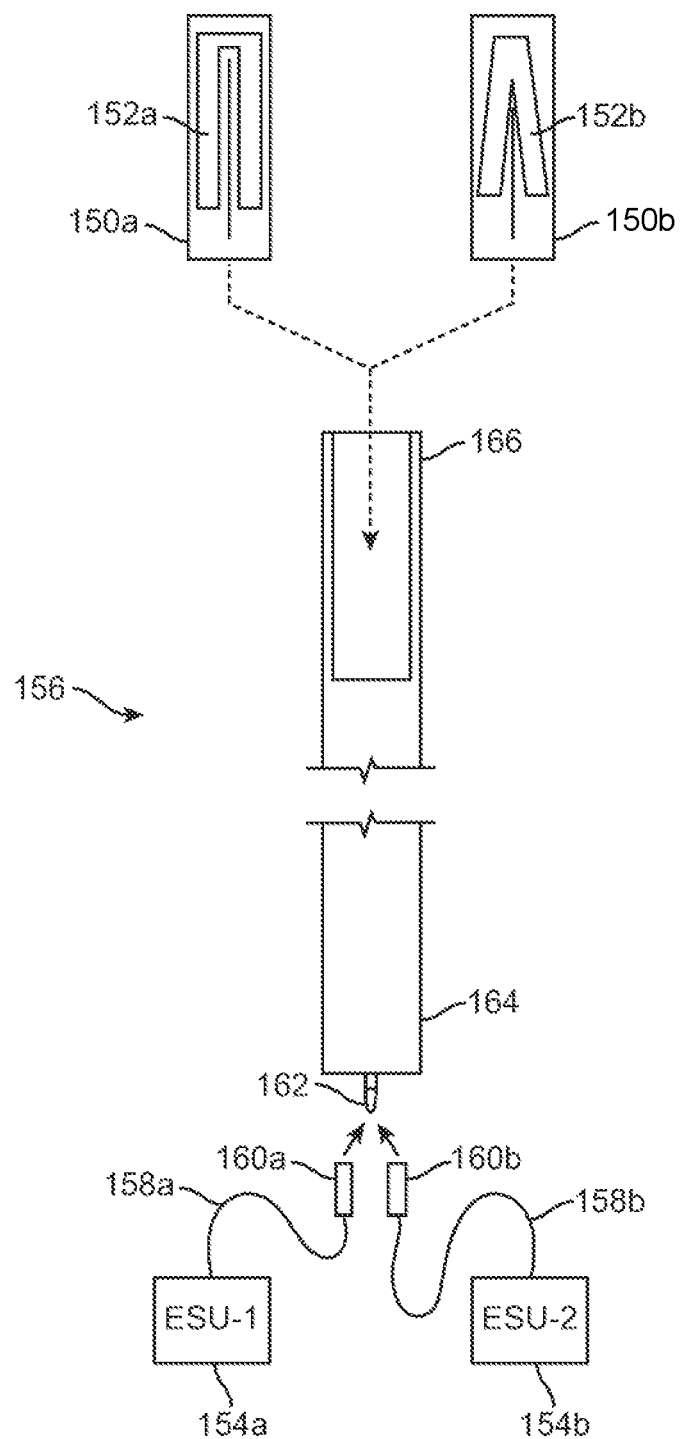
FIG. 7 is a diagrammatic view that illustrates two cartridges, each with a different electrode geometry, that may be removably positioned within a surgical instrument jaw.

In accordance with another aspect of the invention, a sealing instrument is configured to receive removable sealing electrode cartridges, with some cartridges having an electrode geometry for use with one company's ESU and other cartridges having an electrode. geometry for use with another company's ESU. For example, FIG. 7 is a diagrammatic view that illustrates two cartridges, each with a different electrode geometry, that may be removably positioned within a surgical instrument jaw. Cartridge 150a, which may include the various other features described herein, includes an electrode 152a having a geometry designed for use with ESU-1 154a. Thus, when a surgeon has coupled surgical instrument 156 to receive energy from ESU-1 154a (e.g., using a standard cable 158a with a female "banana" type plug 160a that mates as indicated with a corresponding male plug 162 on the proximal end of instrument 156), the associated cartridge 150a is inserted into distal jaw 166 for use. Likewise, cartridge 150b, which also may include the various other features described herein, includes an electrode 152b having a geometry designed for use with ESU-2 154b. ESU-2 154b is different from ESU-1 154a, and so electrode 152b has a geometry designed for use with ESU-2 154b, and this geometry is different from electrode 152a's geometry (the two different shapes shown in FIG. 7 are illustrative of various possible geometries).

When a surgeon has coupled surgical instrument 156 to receive energy from ESU-1 154b (e.g., using a standard cable 158b with a female "banana" type plug 160b that mates as indicated with a corresponding male plug 162 on the proximal end of instrument 156), the associated cartridge 150b is inserted into distal jaw 166 for use.

In accordance with another aspect, cartridges having two or more different architectures may be used with the same ESU. Referring to FIG. 7, for example, the electrode geometries on cartridges 150a,150b may differ from one another, but may be configured for specific sealing tasks when used with the same ESU-1 154a (e.g., one may have a smaller surface area to effectively increase tissue clamping pressure as compared with the other for the same jaw clamping force). As another example, the sealing electrode geometries may be the same on the two cartridges, but one or more other cartridge features, such as those described herein, may differ between the two cartridges (such as changing the cutter geometry, or omitting the cutter, or providing grasping serrations, etc.).

The various electrode geometries shown and described in relation to FIG. 7 are also illustrative of various jaw shapes that may be used for certain specific tissue sealing applications. That is, a surgeon may find that a certain instrument with a certain jaw configuration may be best for a particular task, and so the ESU associated with that instrument is used. But if the surgeon finds that a different instrument manufactured by a different company is best for a different task, then a different ESU must be used. And so aspects of the invention allow at least one jaw (and both, if cartridges are used in both opposing jaws) to be shaped as the surgeon desires without having to use different instruments. The instrument is configured to operate with the desired one or both jaw configuration and the associated ESU.

In the aspects that include various electrode and/or jaw configurations, a system (see e.g., FIGS. 6 and 10 and associated text) may be configured so that cartridge identification information from the integrated circuit chip 42 described above with reference to FIG. 2 may be used to prevent initiating a sealing operation if an improper cartridge and ESU combination exists.

Figure 8A:
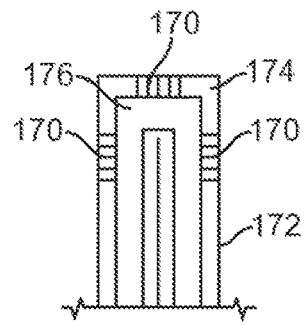
FIGS. 8A-8C are diagrammatic views that illustrate a portion of an electrode cartridge.
Figure 8B:
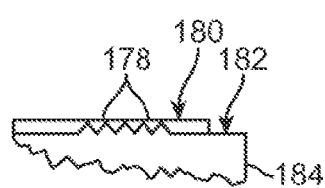
Figure 8C:
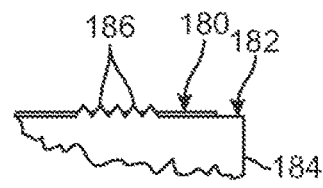
Figure 8D:
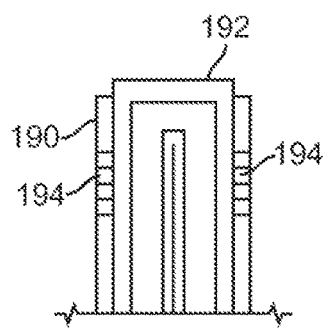
FIGS. 8D-8G are diagrammatic views that illustrate a portion of an electrode cartridge positioned within a surgical instrument jaw.
Figure 8E:
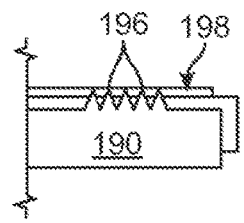

In accordance with another aspect, a cartridge and/or the jaw that receives the cartridge and/or the opposing jaw may be configured to enhance its ability to grasp tissue (e.g., with toothed serrations). Consequently, the surgical instrument may be used for multiple functions—grasping, sealing, and cutting—without requiring removal from its associated access port into the patient. FIGS. 8A-8C are diagrammatic views that illustrate that at least a portion of the cartridge surface opposite the other jaw may be configured to enhance the instrument's tissue grasping ability. As shown in top view FIG. 8A, serrations 170 are placed on the same cartridge 172 surface 174 as electrode 176, and the serrations are positioned around the outside perimeter of the electrode. The serrations shown are illustrative of various configurations that include configuring some or all of the cartridge surface not covered by the electrode to grasp tissue. As shown in side view FIG. 8B, in some embodiments the tops 178 of the serrations may be substantially even with or below the electrode surface 180 (the electrode surface is shown raised above the top surface 182 of the cartridge 184, but it should be understood that the electrode surface may be flush with or even slightly below the cartridge surface). Thus, the instrument's enhanced grasping feature is not used until tissue is clamped at a relatively higher force between the instrument jaws, when the tissue bulges past the electrode surface. Alternatively, as shown in side view FIG. 8C, tops 186 may extend above the electrode surface 180, so that the instrument's enhanced grasping feature is available when tissue is clamped at a relatively lower force between the jaws. It should be understood that the serrations shown in the drawings are illustrative of various features that may enhance the instrument's tissue grasping ability (e.g., various different serration or knurl patterns, raised bumps, small geometric cones, etc.). In some aspects, the electrode surface itself may include the enhanced grasping features so that, for example, an opposing jaw electrode may have ceramic "dots" as described above with reference to FIGS. 3A and 3B, and the cartridge electrode includes serrations. For certain jaw configurations, such an arrangement may provide effective tissue fusion/sealing.

Figure 8F:
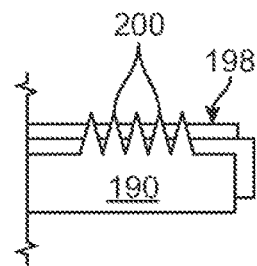
Figure 8G:
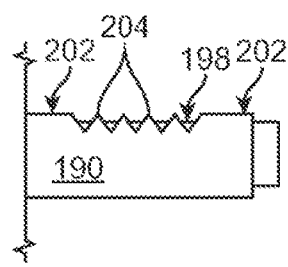

In another aspect, the features used to enhance the instrument's tissue grasping ability are placed on the jaw that receives the cartridge. FIGS. 8D-8G are diagrammatic views that illustrate that at least a portion of the surface of jaw 190 that receives the removable electrode cartridge 192 may be configured to enhance the instrument's tissue grasping ability. As shown in top view FIG. 8D, serrations 194 are placed on at least a portion of the surface of jaw 190 that is opposite the opposing jaw. In a manner similar to that described above with reference to FIGS. 8B and 8C, FIG. 8E illustrates that the tops 196 of the jaw serrations 194 may be substantially flush with or below the top surface 198 of the electrode, which requires a relatively higher jaw clamping force to use the serrations to enhance the instrument's ability to grasp tissue. And, FIG. 8F illustrates that the tops 200 of the serrations may extend above the top surface 198 of the electrode, which requires a relatively lower jaw clamping force to use the serrations to enhance the instrument's ability to grasp tissue. In a similar way, as illustrated in side view 8G, the top surface 198 of the electrode may be below the top surface 202 of the jaw 190 so that the enhanced tissue grasping features 204 engage tissue before the electrode surface engages the tissue. The jaw opposite the jaw that holds the cartridge may also be configured with enhanced tissue grasping features. For example, serrations may be placed on at least a portion of the jaw itself, or they may be placed on at least a portion of the electrode.

In order to achieve an effective tissue seal, the tissue must be clamped between the surgical instrument's electrodes with sufficient force (e.g., in the range of 100-150 psi). Therefore, in another aspect, the instrument is configured with one or more pressure sensors that indicate the clamping force between the opposing jaws. Pressure sensors may be positioned within the removable electrode cartridge, or they may be placed in the instrument jaw that receives the cartridge.

Figure 9A:
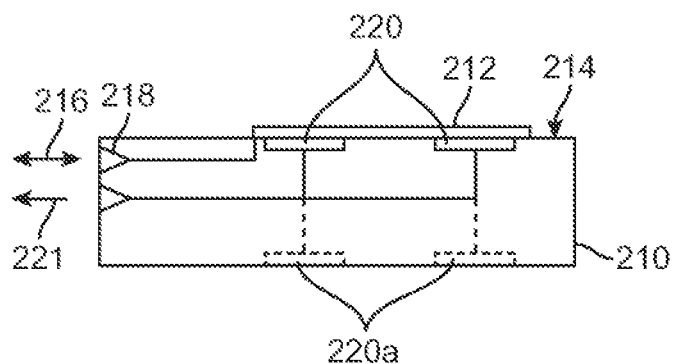
FIGS. 9A and 9B are diagrammatic cross-sectional views that illustrate pressure sensors associated with sensing clamping pressure against an electrode cartridge.
Figure 9B:
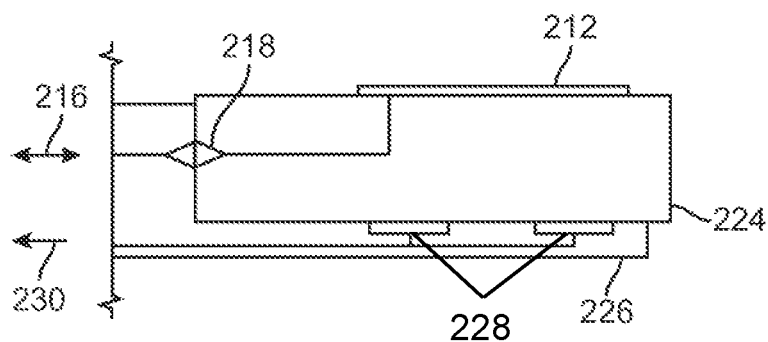

FIGS. 9A and 9B are diagrammatic cross-sectional views that illustrate aspects in which one or more pressure sensors are used to sense jaw clamping pressure. As shown in FIG. 9A, an electrode cartridge 210, which may include the various features described herein, has a tissue sealing electrode 212 positioned at top surface 214, opposite the opposing jaw. Cartridge 210 is received into a distal jaw of the surgical instrument. Electrode 212 receives tissue sealing energy from and provides sealing feedback to its associated ESU, as indicated by arrows 216, via electrical contact 218, which mates with an associated contact in the instrument. One or more pressure sensors 220 are positioned underneath electrode 212, so that sensors 220 sense clamping pressure against electrode 212. Sensors 220 may be placed in various positions in cartridge 210, such as at the bottom side to sense the cartridge's pressure against the jaw receptacle as illustrated by alternate positions 220a, or in other positions within the cartridge that are suitable for measuring the jaw clamping force. Various electrical transducers are suitable for sensors 220, including strain gauges, load cells, force sensitive resistors, etc. Pressure data signals from the one or more sensors 220, as illustrated by arrow 221, are output via electrical contact 222, which mates with an associated contact in the instrument. Alternatively, wireless pressure signal transmission may be used.

As shown in FIG. 9B, an electrode cartridge 224 is received into a distal jaw 226 of the surgical instrument. One or more pressure sensors 228 are positioned at the bottom of the receptacle in the jaw that receives the cartridge (or in any other suitable location in the jaw, such as cartridge support rails), and pressure sensors 228 measure the jaw clamping pressure as the cartridge is pressed against the receptacle. Pressure data signals from the one or more sensors 228, as illustrated by arrow 230, are output to the proximal end of the instrument.

Figure 10:
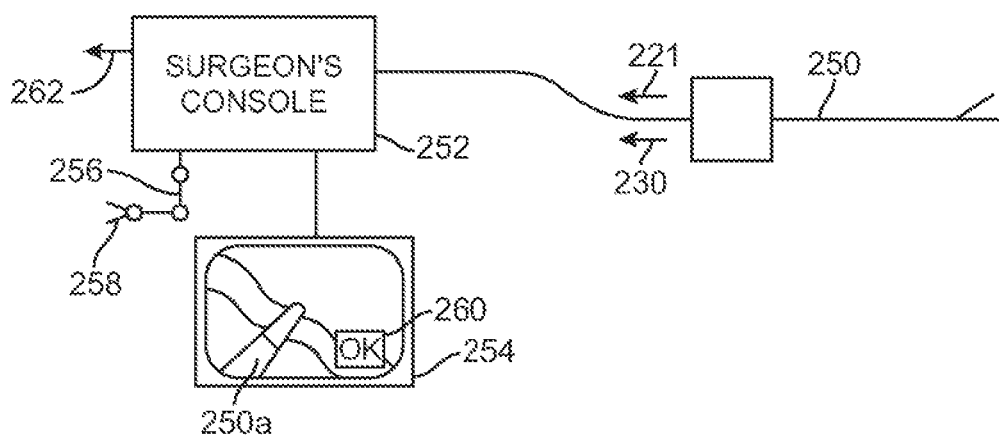
FIG. 10 is a diagrammatic view of a portion of a telerobotic surgical system that provides a closed loop control of clamping pressure for tissue fusion/sealing.

The use of pressure sensors at the distal end of the surgical instrument provides the surgeon with a positive closed loop control of the required clamping pressure needed for effective tissue sealing. FIG. 10 is a diagrammatic view of a telerobotic surgical system that includes a surgical instrument 250 as described herein and a surgeon's console 252. This system is similar to the one illustrated by FIG. 6 and associated text, and various features shown in FIG. 6 are omitted for clarity (i.e., the two figures may be effectively combined to illustrate a single telerobotic surgical system). In an illustrative operation, the surgeon views the distal end of instrument 250 (shown as image 250a) working at a surgical site in a video display 254 associated with surgeon's console. The surgeon teleoperates instrument 250 by using a master controller 256. The surgeon generates a command to close instrument 250's jaws by squeezing pincer assembly 258 on master controller 256. As instrument 250's jaws close around tissue to be manipulated or sealed, surgeon's console 252 receives pressure signals 221,230 (as applicable) from instrument 250 as shown. As the surgeon continues to squeeze pincer assembly 258, the instrument jaws move closer together and then increase clamping force on tissue held between them. When a clamping force sufficient to successfully perform the tissue sealing operation is sensed, an indication is output to the surgeon. Examples of such an indication include a visual indication 260 in the displayed image, an audio indication 262, and a servomotor-induced haptic indication the surgeon feels in master controller 256 (one embodiment of such a haptic indication is akin to the pulse sensation a person feels in certain torque wrench handles when a specified torque is reached by setting a calibrated clutch mechanism), etc. In some aspects, the RF tissue sealing operation may be automatically prevented (with the possibility of manual override in some instances) until an acceptable clamping force is sensed.

Aspects including pressure sensors have been described in the context of a surgical robotic system, but it should be understood that such aspects may be adapted to use within hand-held surgical instruments.

Aspects of the invention have been described herein in various embodiments. To avoid needless repetition, embodiments shown and described in relation to one figure are not necessarily repeated in relation to other figures. It should be understood, however, that whenever possible the various aspects and embodiments described herein may be combined. The claims define the invention.

I claim:
1. A surgical system comprising:
a first cartridge, wherein the first cartridge comprises a first tissue sealing electrode;
a surgical instrument, wherein the surgical instrument comprises:
a first jaw and a second jaw, wherein the first jaw comprises a second tissue sealing electrode facing the second jaw, and wherein the second jaw is configured to removably receive the first cartridge in a position where the first tissue sealing electrode is opposite the second tissue sealing electrode,
wherein at least one of the first jaw and the second jaw further comprises a grasping feature having a textured surface, wherein when the first cartridge is received in the second jaw, the textured surface does not extend into a space between opposing surfaces of the first tissue sealing electrode and the second tissue sealing electrode;
a tissue cutter operably coupled to translate relative to the first jaw and second jaw; and
a controller operably coupled to the surgical instrument, wherein the controller is programmed to:
generate a command to actuate the surgical instrument to perform a tissue sealing procedure including supplying energy to the first and second tissue sealing electrodes,
generate a command to actuate the surgical instrument to cease the tissue sealing procedure and to perform a cutting procedure by translating the tissue cutter in response to a sensor detecting completion of the tissue sealing procedure, and
generate a command to reduce a clamping pressure between the first and the second jaws in response to sensing completion of the cutting procedure.

2. The surgical system of claim 1, further comprising a second cartridge, wherein:
the first tissue sealing electrode has a first geometry; and
the second cartridge comprises a third tissue sealing electrode having a second geometry different from the first geometry.

3. The surgical system of claim 2, wherein the second jaw is configured to interchangeably and removably receive the first cartridge and the second cartridge.

4. The surgical system of claim 3, further comprising:
a first electrosurgical unit operably coupled to provide tissue sealing energy to the second tissue sealing electrode and the first tissue sealing electrode when the first cartridge is positioned in the second jaw; and
a second electrosurgical unit operably coupled to provide tissue sealing energy to the second tissue sealing electrode and the third tissue sealing electrode when the second cartridge is positioned in the second jaw.

5. The surgical system of claim 1, further comprising at least one pressure sensor positioned to sense information indicative of the clamping pressure exerted by the first and second jaw on tissue positioned between the first and second tissue sealing electrodes.

6. The surgical system of claim 5, wherein the controller comprises a surgeon console configured to provide output indicating that a pressure sufficient for an effective tissue sealing operation exists between the first and second tissue sealing electrodes, wherein the surgeon console is configured to provide the output based on the at least one pressure sensor sensing the sufficient pressure.

7. The surgical system of claim 5, wherein the controller is further programmed to generate the command to actuate the surgical instrument to perform a tissue sealing procedure in response to receiving from the pressure sensor sensed information indicative of a predetermined clamping pressure exerted by the first and second jaws.

8. The surgical system of claim 1, wherein the second jaw is stationary and the first jaw is movable during tissue sealing.

9. The surgical system of claim 1, wherein the tissue cutter is disposed on the first cartridge.

10. The surgical system of claim 9, wherein:
the first cartridge is elongated in a direction between first and second ends of the first cartridge, and
the tissue cutter is movable along a direction of elongation and relative to the first cartridge.

11. The surgical system of claim 9, wherein the tissue cutter comprises a movable blade.

12. The surgical system of claim 9, wherein the tissue cutter comprises a third electrode.

13. The surgical system of claim 1:
wherein the first cartridge further comprises an electronic encryption device, the electronic encryption device being configured to store information relating to first cartridge use.

14. The surgical system of claim 1, further comprising a wrist mechanism that couples the first and second jaws to a shaft and provides at least a pitch or yaw degree of freedom relative to the shaft for the first and second jaws.

15. The system of claim 1, further comprising a remote input mechanism operably coupled to the controller.

16. The system of claim 1, wherein the textured surface of the grasping feature is chosen from at least one of knurling, serrations, raised bumps, teeth and cones.

* * * * *